United States Patent
Plank

(10) Patent No.: US 7,025,937 B2
(45) Date of Patent: Apr. 11, 2006

(54) APPARATUS AND METHOD FOR IMMUNOLOGICAL LABELING FOR THIN TISSUE SECTIONS

(75) Inventor: Heinz Plank, Wr. Neudorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 0 days.

(21) Appl. No.: 10/789,529

(22) Filed: Feb. 27, 2004

(65) Prior Publication Data

US 2004/0171102 A1 Sep. 2, 2004

(30) Foreign Application Priority Data

Feb. 28, 2003 (DE) ................. 103 09 211

(51) Int. Cl.
*B01L 3/00* (2006.01)

(52) U.S. Cl. .............. 422/102; 422/99; 422/100; 422/102; 422/68.1; 422/58; 435/286.3; 435/287.3; 435/309.1; 435/284.1

(58) Field of Classification Search .......... 422/99–100, 422/102, 68.1, 58; 436/174; 435/286.3, 435/287.3, 309.1, 284.1
See application file for complete search history.

(56) References Cited

U.S. PATENT DOCUMENTS

| 5,079,172 A | 1/1992 | Hari et al. |
| 5,143,714 A | 9/1992 | Cosgrove et al. |

FOREIGN PATENT DOCUMENTS

| DE | 3878167 | 5/1993 |
| DE | 29817912 | 3/1999 |
| DE | 29906382 | 11/1999 |
| EP | 0317001 | 2/1993 |

*Primary Examiner*—Jill Warden
*Assistant Examiner*—Jyoti Nagpaul
(74) *Attorney, Agent, or Firm*—Simpson & Simpson, PLLC

(57) ABSTRACT

An apparatus and a method for immunological labeling of thin tissue sections are disclosed. The treatment fluid is applied in the form of liquid droplets onto at least one slide, the arrangement of liquid droplets corresponding to the arrangement of the thin tissue sections on the carrier plate. Each slide is retained in a transport container, the transport container being embodied in the form of a trough which comprises a peripheral delimiting wall that is closed off by a base. The base of one transport containers constitutes the cover of a transport container arranged beneath it. The transport containers are stacked in a first and a second station.

11 Claims, 9 Drawing Sheets

APPARATUS AND METHOD FOR IMMUNOLOGICAL LABELING FOR THIN TISSUE SECTIONS

CROSS REFERENCE TO RELATED APPLICATIONS

This application claims priority of the German patent application 103 09 211.0, which is incorporated by reference herein.

FIELD OF THE INVENTION

The present invention concerns an apparatus for immunological labeling for thin tissue sections. In particular, the invention concerns an apparatus for immunological labeling of thin tissue sections having a carrier plate on which the thin tissue sections are affixed in a defined pattern, and having at least one slide on which the treatment liquid is applied in the form of liquid droplets, the arrangement of the liquid droplets corresponding to the arrangement of the thin tissue sections on the carrier plate.

The present invention furthermore concerns a method for immunological labeling for thin tissue sections.

BACKGROUND OF THE INVENTION

To allow examination of the structure of biological samples such as tissues or cells using an electron microscope or high-resolution optical microscope methods, ultrathin sections (only a few nm thick) are prepared and are applied onto specimen carrier grids (hereinafter referred to as metal grids) made of metal, preferably of nickel. For microscopic examination the sections are contrasted, or individual constituents of the sample are labeled using special cytochemical methods. These cytochemical methods are often based on the principle of ligand pair formation: a first ligand can be contained in the biological sample, and the second ligand, when it comes into contact with that sample, then binds as a binding partner to the first ligand. Examples of biologically based ligand pairs include antigen/antibody binding pairs, enzyme/substrate binding pairs, lectins/sugars, hormone/receptor systems, and DNA/DNA and DNA/RNA pairs.

Numerous methods involving the antigen/antibody binding pair are known in the existing art; these are grouped under the heading of immunohistochemistry and immunocytochemistry (hereinafter referred to as immunological labeling techniques). U.S. Pat. No. 5,143,714, for example, discloses a method that adsorbs an antigen out of a liquid sample in a pelletizable gel substance. The gel pellet is surrounded by a diffusion barrier, integrated as a block into a stamped-out gel matrix, and subsequently subjected to immunological labeling techniques just like a tissue sample. German Pat. No. DE 38 78 167 T2 describes the use of colloidal gold particles to label ligands, using the immunogold staining technique. A greatly improved method that permits qualitative and quantitative evaluation of an antigen in a sample is disclosed in U.S. Pat. No. 5,079,172 in the form of a sandwich assay, in which the first antibody that binds the antigen is labeled with a gold-labeled second antibody that binds the first antibody. Using electron-microscopy evaluation methods, the antigen the sample can be determined qualitatively and quantitatively based on the quantity of gold particles.

A characteristic shared by many immunohistochemical and immunocytochemical protocols for immunological labeling of thin tissue sections is the fact that they usually comprise ten to 20 individual process steps. Most of the process steps comprise operations in which the sample under examination is washed with a buffer solution or labeling solution.

At present, these washing operations are performed manually, in a laborious process in which individual droplets of the aqueous buffer solution or labeling solution are applied with a pipette onto a hydrophobic substrate (e.g. Parafilm®, Parlodion®, Colloidion, or Formfan®). The metal grids with the thin tissue sections are individually laid down thereon in order to react with the treatment liquid. Because of the light weight of the metal grid and the surface tension of the liquid droplet, the metal grid floats on the droplet surface. After a certain residence time for this step (often 5 to 10 min), the metal grid is transported with tweezers to the next droplet. This operation is continued up to the last position of the standard protocol, and occupies a technician for as long as several hours for each immunological labeling reaction.

It is readily apparent that this manual process requires constant attention by the operator, and entails high labor costs because of the large time requirement. The number of samples to be processed simultaneously is greatly limited, and errors by the operator while precisely pipetting and positioning liquid droplets with very small volumes cannot be excluded. The manual method cannot rule out confusion of samples after the long processing time during immunological labeling; this could be prevented by using a sample carrier having an identifier in the form of a chip or barcode, as presented in German Utility Model DE 299 06 382 U1.

In addition, evaporation of the liquid droplets during longer-duration standard protocols constitutes a major problem.

Although German Utility Model DE 298 17 912 U1 discloses an apparatus for washing microscopable preparations on supports after immunocytochemical treatment, it refers to a wash box in which a larger quantity of washing solution flows through at a certain flow rate over the preparation and carrier. This apparatus is not suitable for the implementation of immunological labeling techniques themselves, since the antibody-containing labeling solutions that are used are very expensive and are therefore employed in only the smallest possible volumes.

An apparatus and method that implement in fully automatic fashion the operation of carrying out immunological labeling techniques for thin tissue samples are not presently known.

SUMMARY OF THE INVENTION

It is therefore the object of the invention to make available an apparatus for immune labeling of thin tissue sections which effectively permits multiple thin tissue sections to be processed simultaneously with reproducible quality, fully automatically and according to an individually definable protocol, and with no intervention by the operator.

The object is achieved by an apparatus for immunological labeling of thin tissue sections, comprising: a carrier plate on which the thin tissue sections are affixed in a defined pattern; at least one slide on which a treatment liquid is applied in the form of droplets, wherein the arrangement of the droplets on the slide corresponds to the arrangement of the thin tissue sections on the carrier plate; a transport container for holding one slide; wherein the transport container has a peripheral delimiting wall attached to a base; and a first and a second station, in which the transport containers are stacked, wherein the base of one transport container constitutes the cover of a transport container arranged beneath it.

A further object of the invention is to make available a method for immune labeling of thin tissue sections which effectively permits multiple thin tissue sections to be processed simultaneously with reproducible quality, fully automatically and according to an individually definable protocol, and with no intervention by the operator.

This object is achieved, according to the present invention, with a method that comprises the steps of:

a) creating an individual treatment process for the thin tissue sections, which are arranged on a carrier plate that is inserted in a treatment section;

b) applying droplets onto a plurality of slides, each of which has multiple depressions for reception of the liquid droplets;

c) placing the slides, together with a transport container provided for the slide, in a first station;

d) transferring the transport container, together with the slide, from the first station to a treatment section by means of a transport mechanism;

e) lifting the transport container, together with the slide, in such a way that the liquid droplets on the slide wet the thin tissue sections on the carrier plate;

f) transferring the transport container together with the slide, at a time predetermined by the individual treatment process, to a second station that holds used slides; and g) performing steps d) through f) until all the slides provided in the first station for an individual treatment process have been removed.

The apparatus according to the present invention is particularly advantageous because the apparatus is equipped with a carrier plate on which the thin tissue sections are affixed in a defined pattern. Also provided is at least one slide on which the treatment liquid is applied in the form of liquid droplets, the arrangement of the liquid droplets corresponding to the arrangement of the thin tissue sections on the carrier plate. Each of the slides that is equipped with liquid droplets is introduced into a transport container. The transport container is embodied in the form of a trough, the trough comprising a peripheral delimiting wall that is closed off by a base. The base (50) of one transport container is the cover of a transport container arranged beneath it. The transport containers are stacked in a first and a second station (20, 21). Stacking of the transport containers is particularly advantageous because evaporation of the liquid droplets applied on the slide is thereby prevented. To ensure a certain moisture level in the enclosed space around the slides, a moisture-emitting medium is placed in the transport container.

Stacked in the first station are the transport containers each carrying a slide which is equipped with a plurality of liquid droplets and which has not yet been brought into contact with the thin tissue sections on the carrier plate. Stacked in the second station are the transport containers each carrying a slide which has already been brought into contact with the thin tissue sections on the carrier plate. These slides are exhausted, and are stacked together with the transport containers in the second station until the entire treatment process is complete. After completion of the treatment process, the transport containers and/or slides can be subjected to a cleaning process for later use.

Multiple metal grids are mounted on the carrier plate, so that the number of samples or thin tissue sections to be processed simultaneously is greatly increased. For treatment of the thin tissue sections, the slides provided in transport containers are brought successively, in accordance with the procedure required for the individual treatment process, into defined contact with the carrier plate so that the thin tissue section is wetted with the treatment liquid. The purpose here is to move the requisite slide into the treatment position with respect to the carrier plate.

The apparatus possesses the further advantage that it is constructed from an input section, a station section, and a treatment section. A transport mechanism travels back and forth between the station section and the treatment section, in order to transport a transport container from the station section to the treatment section or from the treatment section to the station section. The input section encompasses a user interface having multiple input buttons and a display. The user can individually configure the treatment process using the input buttons.

The method according to the present invention is advantageous because an individual treatment process for the thin tissue sections is created. The carrier plate having the thin tissue sections is inserted into a treatment section. The application of liquid droplets onto a plurality of slides, each of which has multiple depressions for reception of the liquid droplets, is accomplished with a multi-channel pipette. The slides are stored, together with a transport container provided for the slide, in a first station. For the treatment process, the slides are transferred by a transport mechanism from the first station to a treatment section. The transport containers, together with the slide, are lifted by the transport mechanism in such a way that the liquid droplets on the slide wet the thin tissue sections on the carrier plate. After complete of the time during which the thin tissue sections must be wetted with the treatment liquid, the transport containers together with the slides are transferred to the second station.

Further advantageous embodiments of the invention are evident from the dependent claims.

BRIEF DESCRIPTION OF THE DRAWINGS

The invention will be elucidated below with reference to the examples depicted schematically in the Figures, in which:

FIG. 11 is a sectioned view of the transport container along the dashed line A—A depicted in FIG. 10a.

DETAILED DESCRIPTION OF THE INVENTION

Figure 1:
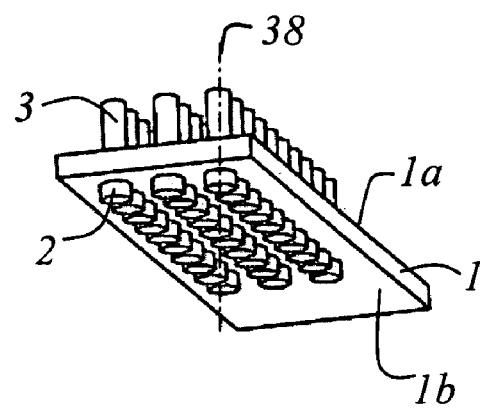
FIG. 1 is a perspective view of a carrier plate that carries metal grids.

FIG. 1 shows a carrier plate 1 that defines an upper side 1a and a lower side 1b. On lower side 1b, carrier plate 1 possesses marked positions at which metal grids 2 having thin tissue sections 2a (see FIG. 3) are positioned. The positions of metal grids 2 on carrier plate 1 are elevated. This prevents liquid bridges from forming between the individual metal grids 2 upon contact with the liquid droplets. Located on upper side 1a of carrier plate 1, opposite the positions of metal grids 2, are orifices 3a (see FIG. 3) which contain magnets 3, for example permanent magnets. They cause metal grids 2 to be held in place on lower side 1b of carrier plate 1 by magnetic force. The spacing between metal grid 2 and magnet 3 should be kept as small as possible (<2 mm). Carrier plate 1 is preferably made of a dimensionally stable nonmagnetic material, preferably aluminum, brass, or fiber-reinforced plastics, and advantageously is hydrophobically coated (e.g. with a Teflon pressure coating) on lower side 1b that carries metal grids 2. It is self-evident to one skilled in the art that numerous embodiments are possible in terms of the shape of carrier plate 1 and the arrangement of metal grids 2 on carrier plate 1. In the embodiment depicted here, a rectangular plate having dimensions of approx. 76×26 mm (3×1 inch; microscope slide size) accommodates, for example, 10×3 metal grids 2 having a diameter of 3 mm. It is critical that the positions of metal grids 2 on lower side 1b of carrier plate 1 be located opposite the orifices for magnets 3 on upper side 1a of carrier plate 1, and preferably also be located opposite the positions of at least one liquid droplet 6 on upper side 4a of a slide 4 (see FIG. 2).

In a further exemplary embodiment, metal grids 2 are held on lower side 1b of carrier plate 1 by electromagnets (not depicted).

Figure 2:
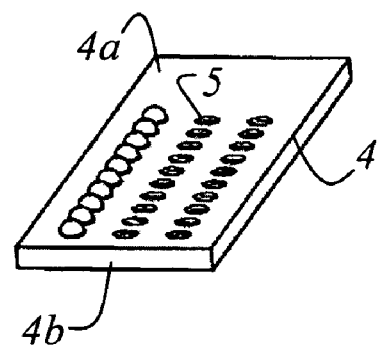
FIG. 2 is a perspective view of a slide having depressions that can be filled with at least one treatment liquid.

FIG. 2 is a perspective view of slide 4 according to the present invention, which defines an upper side 4a and a lower side 4b. Slide 4 possesses on upper side 4a multiple depressions 5 (called "wells") that, in the embodiment shown, are arranged in rows and are each filled with a liquid droplet 6. Liquid droplet 6 comprises a washing solution or treatment solution as disclosed in the existing art. Provision is also made for different liquids to be present in the individual depressions 5 (e.g. one row of depressions 5 filled with washing solution, the next row of depressions 5 filled with labeling solutions having various antibodies). Slide 4 is advantageously transparent and is made of dimensionally stable material. Slide 4 is preferably made of glass or plastic, and is hydrophobically coated (e.g. with a Teflon pressure coating 5a) on upper side 4a that carries depressions 5 and in depressions 5 themselves. Depression 5 is identical in depth to thickness D (see FIG. 3) of Teflon coating 5a. Depression 5 is advantageously approx. 50 μm in size. Depressions 5 carry liquid droplets 6 having a volume that varies between 50 μl and 5 μl. The volume of liquid droplets 6 for washing solution is greater than the volume of the liquid droplets that contain antibodies and/or gold. The reason for the reduced volume with antibodies or gold solution is that the cost of such solutions is high. The Teflon pressure coating is the same for the various droplet sizes. Liquid droplets 6 bulge upward to a greater or lesser extent because of the hydrophobic rim coating. In order to bring the grids into contact with these droplets, it is absolutely necessary in terms of the procedure to know the droplet size, since the droplet size results in a different position for the lowering motion of metal grids 2.

Figure 3:
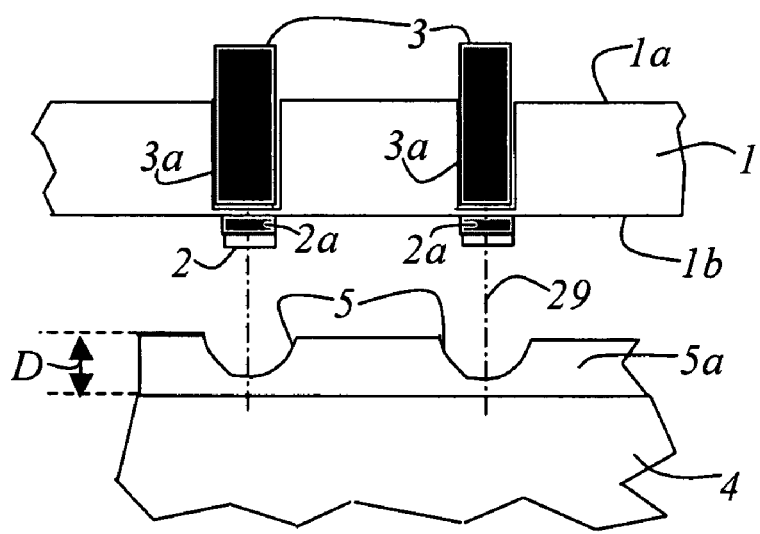
FIG. 3 is a schematic sectional view that illustrates the spatial correlation of the carrier plate with the slide.

The spatial correlation between slide 4 and carrier plate 1 is depicted in FIG. 3 in a partial cross-sectional view. The partial cross-sectional view is defined, for example, in FIG. 2 by dashed line 38. In the exemplary embodiment shown here, a hydrophobic coating 5a having a thickness D is applied on slide 4. Orifices 3a for magnets 3 are provided in carrier plate 1. Samples or thin tissue sections 2a are provided at marked positions on lower side 1b of carrier plate 1. Adjoining each thin tissue section 2a is a metal grid 2. Metal grid 2, and thus also thin tissue section 2a, are held in position by the associated magnets 3. Dot-dash line 29 in FIGS. 1 and 3 illustrates the fact that carrier plate 1 and slide 4 are arranged in such a way that each thin tissue section 2a with metal grid 2 lies opposite a depression 5 on slide 4.

Figure 4A:
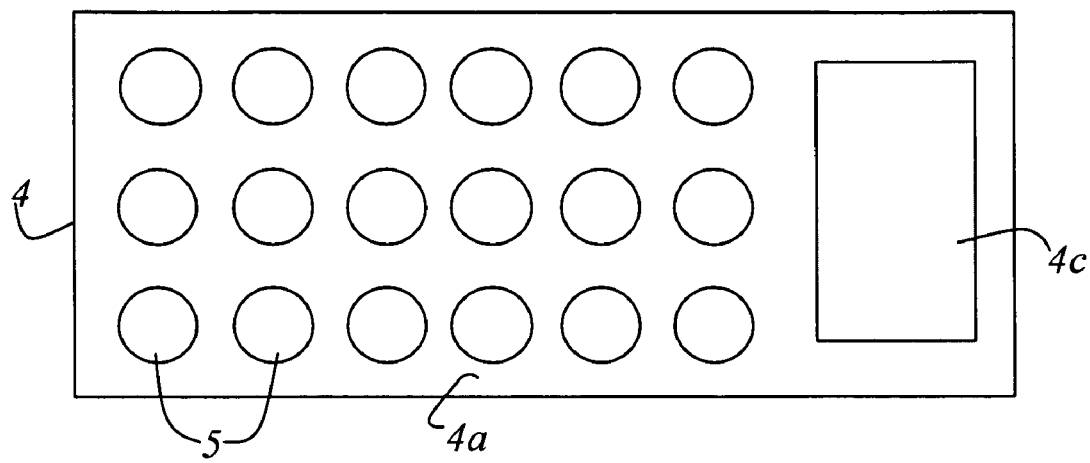
FIG. 4a is a plan view of an embodiment of a slide.
Figure 4B:
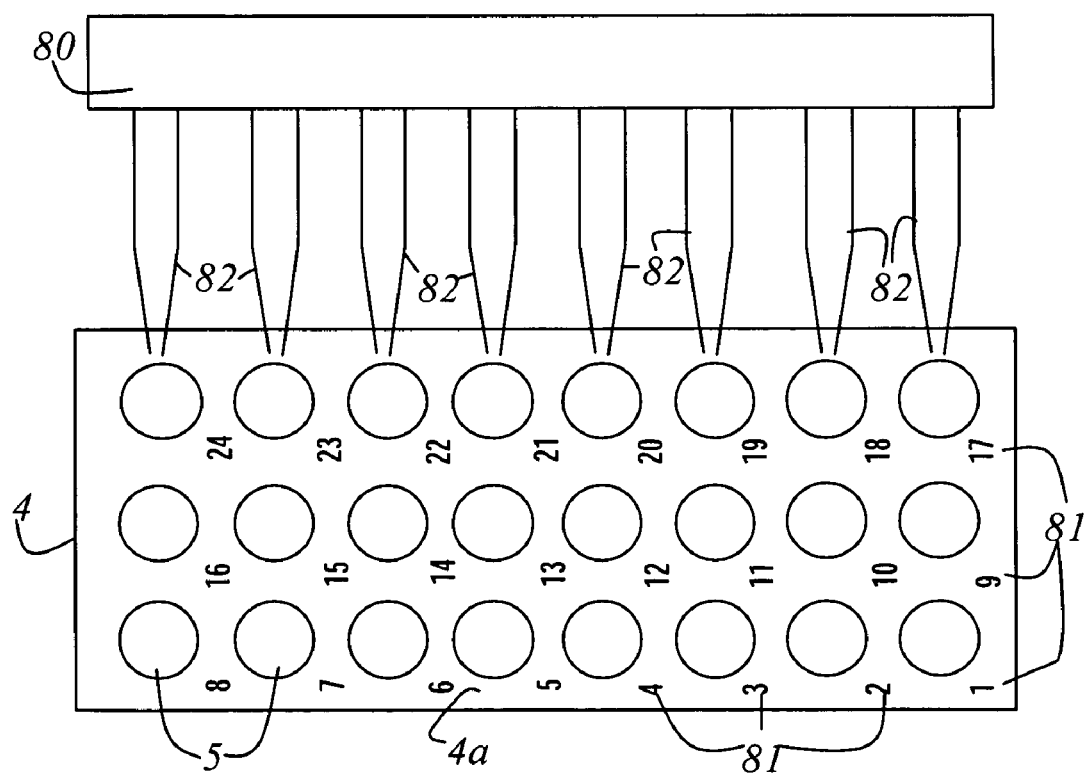
FIG. 4b is a plan view of a further embodiment of a slide, a pipette for the application of liquid droplets likewise being depicted.

FIG. 4a shows an embodiment of a slide that is used in the context of the invention. For identification, slide 4 advantageously possesses an identifier such as the one depicted, for example, in German Utility Model DE 299 06 382 U1. Identifier 4c is mounted on surface 4a of slide 4 and can be embodied in the form of a barcode, transponder, or chip. It is evident to one skilled in the art that numerous possible embodiments exist in terms of the size and shape of slide 4 and the arrangement of depressions 5 on upper side 4a of slide 4. A further embodiment of slide 4 is depicted in FIG. 4b. A rectangular surface of slide 4 having the dimensions 76 mm×26 mm contains, in the Teflon coating of the slide, 8×3 depressions 5 having a diameter of 2 to 3 mm. For recording purposes, a number 81 is associated with each depression 5. Also depicted in FIG. 4b is a multi-channel pipette 80 which allows a defined application of liquid droplets 6 onto slide 4. In addition, the requisite liquid volume can be set very precisely with multi-channel pipette 80, and the application of liquid droplets 6 onto the slide is particularly effective. Since slide 4 possesses three rows each having eight depressions 5, multi-channel pipette 80 likewise has eight individual channels 82, spaced in accordance with depressions 5 on slide 4.

Figure 5:
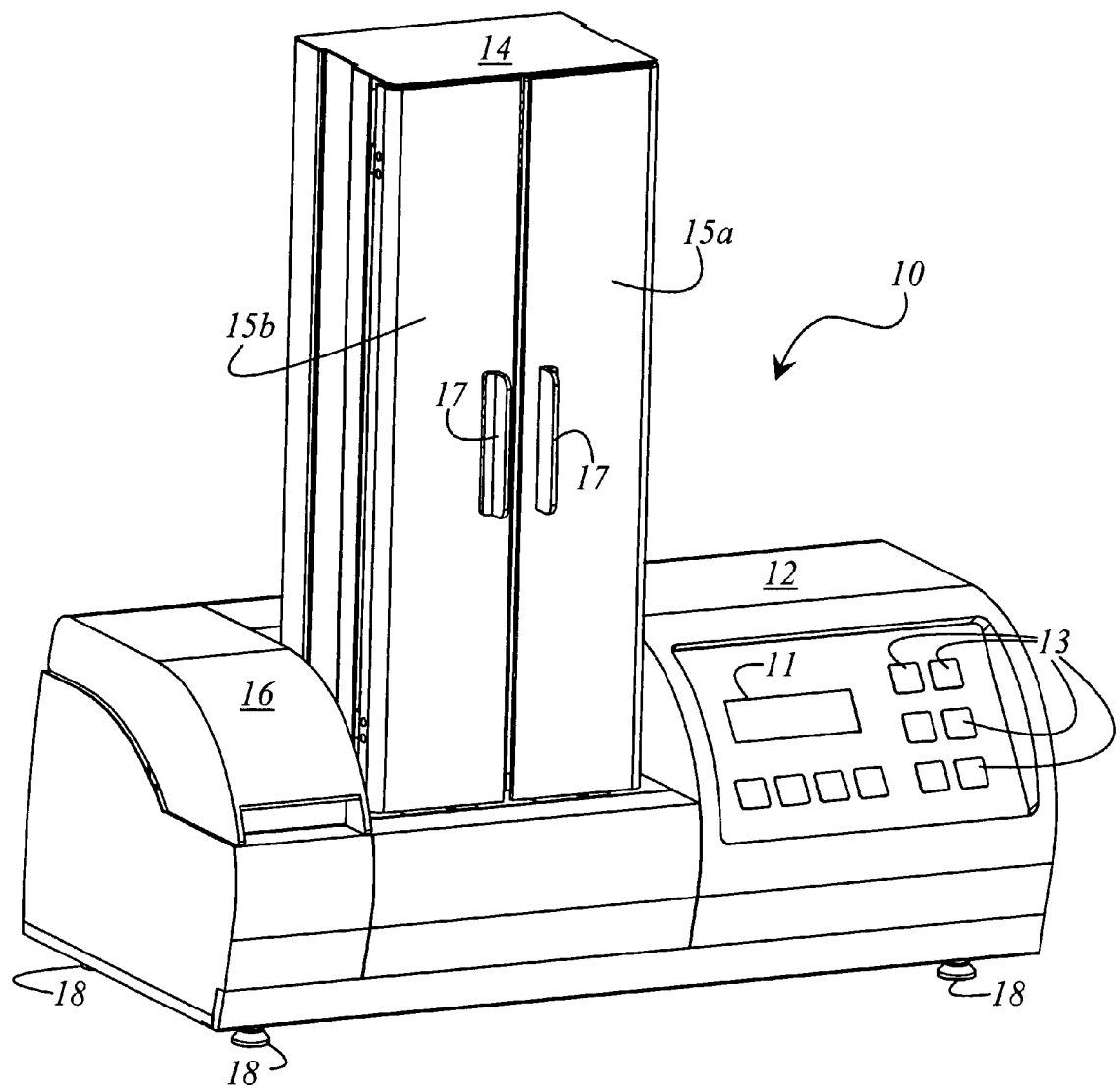
FIG. 5 is a perspective view of the entire apparatus for immune labeling of thin tissue sections.

FIG. 5 is a perspective view of the entire apparatus 10 for immune labeling of thin tissue sections. Apparatus 10 is configured in such a way that all the processes and transport operations occurring in the interior of the apparatus are closed off from the environment. The apparatus is made up substantially of an input section 12, a station section 14, and a treatment section 16. The apparatus moreover encompasses the electronics and software necessary for control and regulation purposes. Input section 12 comprises a user interface 22 having multiple input buttons 13 and a display 11 (see the description of FIG. 11 for a more detailed explanation). Using input buttons 13, the user can create an individual protocol for treating the thin tissue sections. Via display 11, the user receives a response to his or her inputs or can be informed about the process status inside apparatus 10. Station section 14 possesses a first and a second door 15a and 15b through which the user can load apparatus 10 with slides 4 that carry multiple liquid drops 6, or can remove slides 4 exhausted by the process. Through first door 15a, slides 4, each arranged individually in a transport container (see FIG. 10) for transport, can be introduced into station section 14. Through second door 15b, the exhausted slides 4, each arranged individually in a transport container, can be removed from station section 14. Each door 15a and 15b can be opened and closed with a handle 17. Several feet 18 are provided on apparatus 10 in order to space apparatus 10 away from an installation surface.

Figure 6:
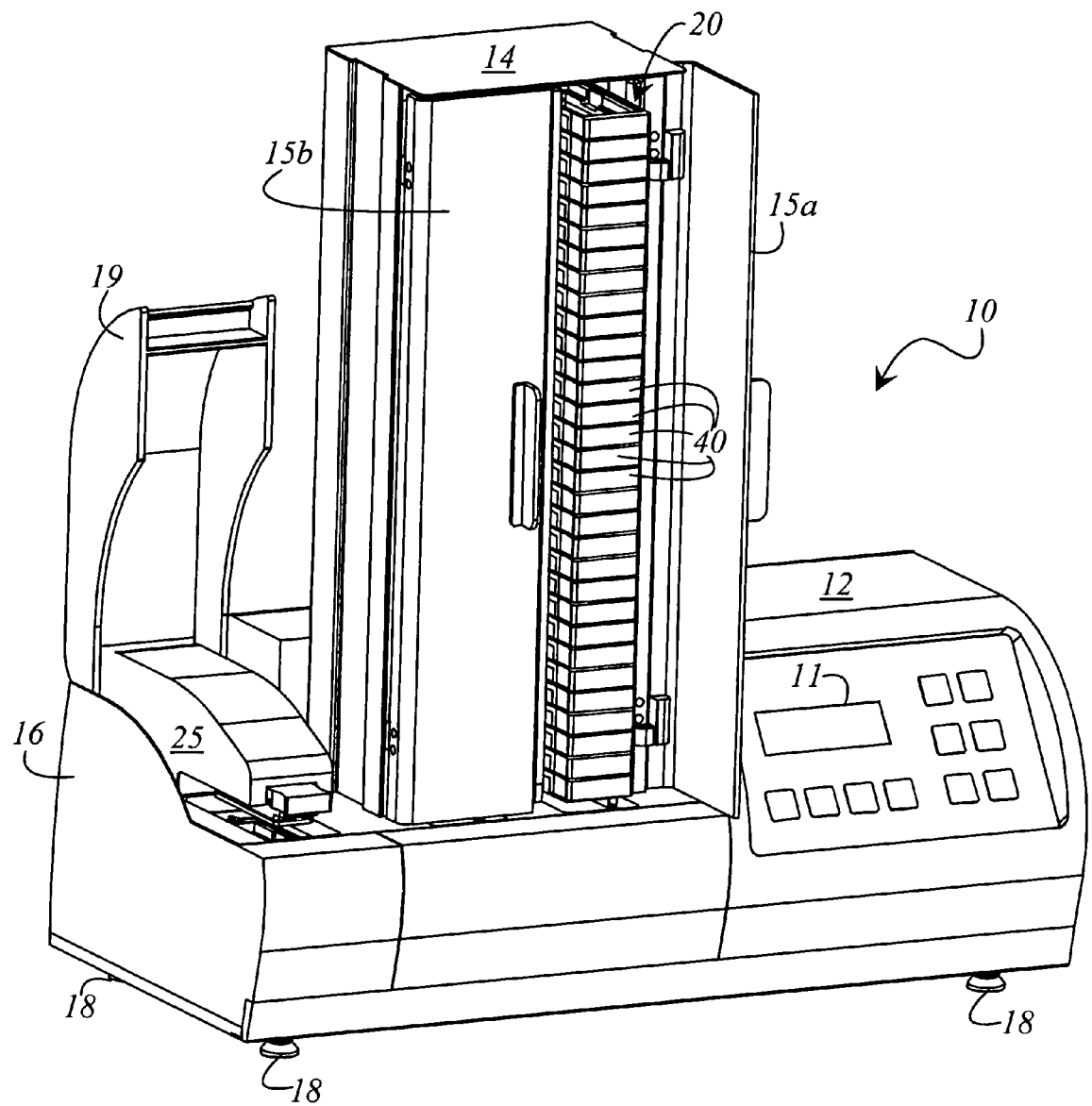
FIG. 6 is a perspective view of the entire apparatus for immune labeling of thin tissue sections, in which some housing parts have been opened in order to provide a view into the interior of the apparatus.

FIG. 6 is a perspective view of the entire apparatus 10 for immune labeling of thin tissue sections, in which first door 15a of station section 14 and a cover 19 of treatment section 16 have been opened in order to provide a view into the interior of apparatus 10. A first station 20 with multiple transport containers 40 is provided behind first door 15a of station section 14. Provided in each of transport containers 40 is a slide 4 having multiple liquid droplets in each case, which are conveyed for the treatment of tissue sections in treatment section 16. A staining unit 25 is provided in treatment section 16. In staining unit 25, carrier plate 1 having the tissue sections is brought successively into contact with different slides 4. Slides 4 are transported to staining unit 25 according to an individual protocol, and the contact time with the tissue sections is likewise determined according to the individual protocol.

Figure 7:
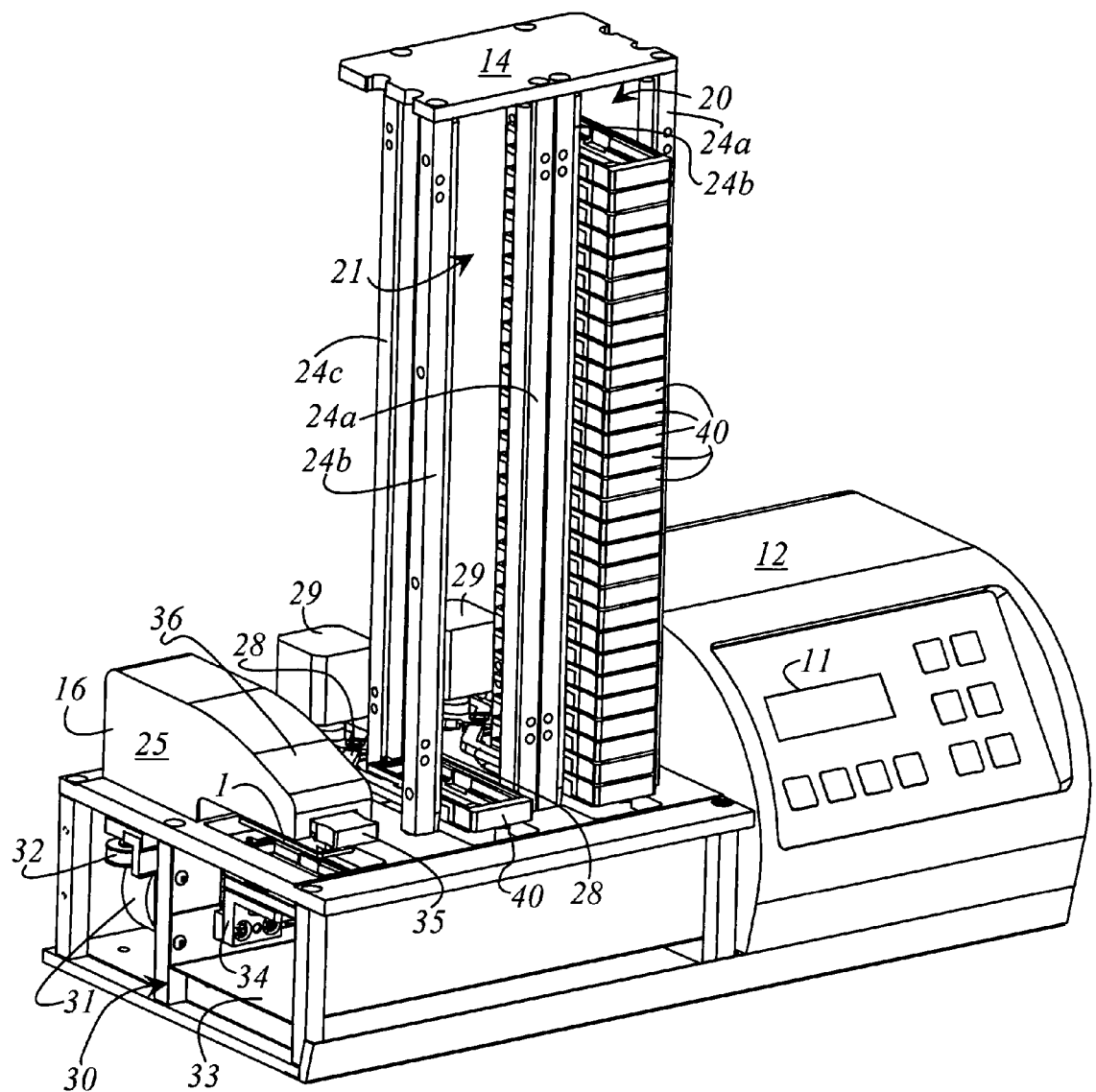
FIG. 7 is a perspective view of the entire apparatus for immune labeling of thin tissue sections, in which some housing parts have been removed in order to provide a better view into the interior of the apparatus.

FIG. 7 is perspective view of the entire apparatus 10 for immune labeling of thin tissue sections, in which pivotable cover 19 of treatment section 16 and the housing for station section 14 have been removed. Station section 14 encompasses a first station 20 and a second station 21. As already mentioned, first station 20 accommodates transport containers 40 with slides 4 before contact with the tissue sections. Transport containers 40 with slides 4 are conveyed to second station 21 after they have been in contact with the tissue section. First station 20 and second station 21 are constituted by a first, second, and third bar 24a, 24b, and 24c which are parallel to one another. First and second bars 24a and 24b are the endpoints of the rails of an isosceles triangle. Third bar 24c is the vertex of the isosceles triangle. First, second, and third bars 24a, 24b, and 24c serve as guides for transport containers 40. Bars 24a, 24b, 24c are secured at their upper ends in a common plate 26. This plate 26 thus limits the stacking height of transport containers 40. At the lower end of bars 24a, 24b, 24c, each stack of transport containers 40 is held by a clamp 28. Associated with each clamp 28 is a motor 29 that opens and closes clamp 28.

Apparatus 10 possesses a delivery unit 30. Station section 14 and treatment section 16 are arranged on delivery unit 30. In delivery unit 30, transport containers 40 are transported from first station 20 to treatment section 16, and from treatment section 16 to second station 21. Provided in delivery unit 30 are at least one motor 31 and one transport means 32, which effects transport of transport containers 40 to the various units. Transport means 32 can be embodied, for example, in the form of a toothed belt.

A carrier plate 1 is provided in treatment section 16. Carrier plate 1 is insertable into a holder 35, together with which carrier plate 1 is slidable into an arm 36 of treatment section 16. Delivery unit 30 has a delivery conduit 33 that extends beneath carrier plate 1 held in arm 36, and beneath first and second stations 20 and 21. In delivery conduit 33, transport holder 34 is movable back and forth between first and second stations 20 and 21 and treatment section 16.

Figure 8:
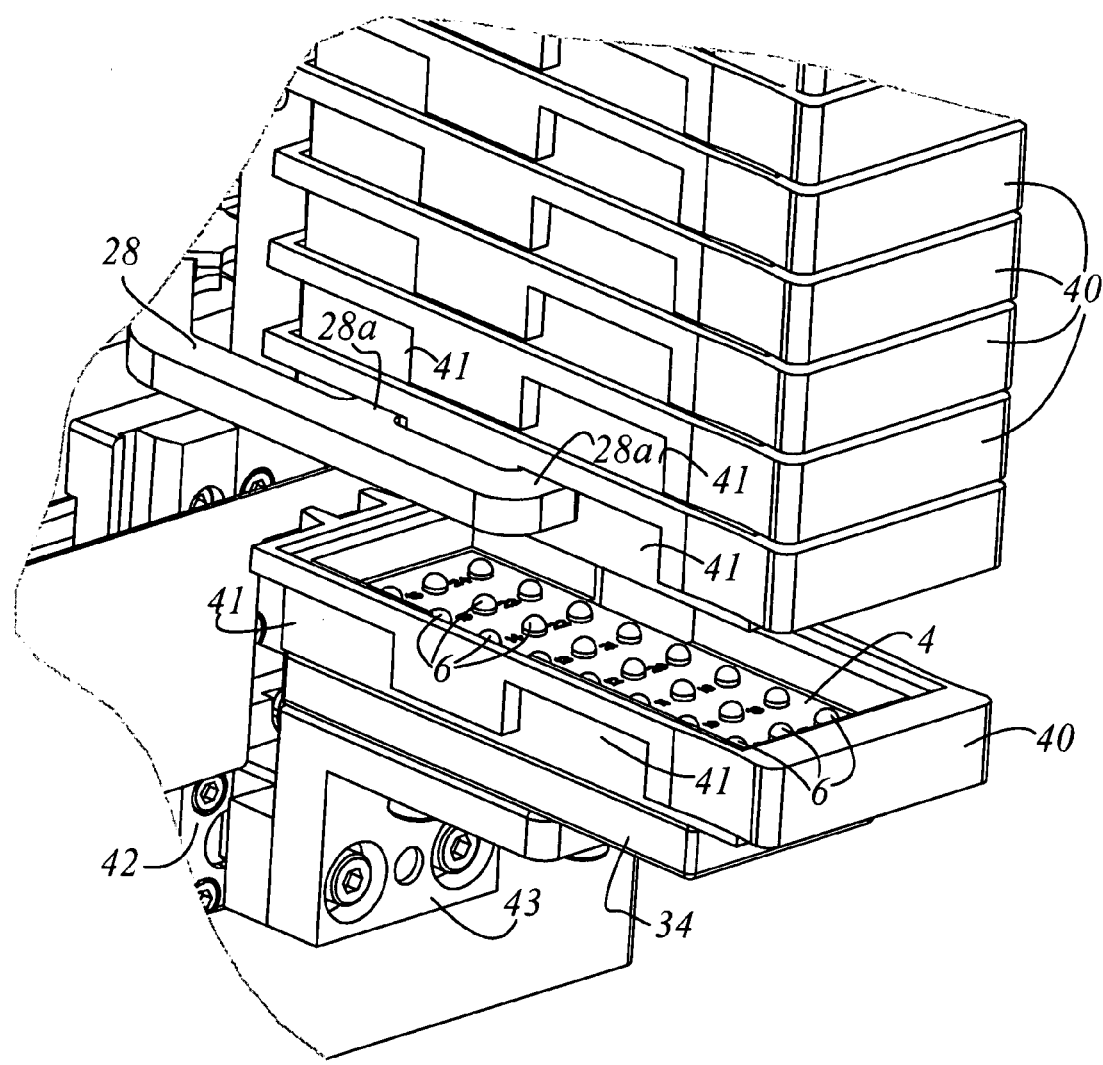
FIG. 8 is a perspective detail view of the coaction of the transport holder with the stack of transport containers in the first or second station.

FIG. 8 is a perspective detail view of the coaction of transport holder 34 with the stack of transport containers 40 in first or second station 20 and 21. As already mentioned in FIG. 6, the stack of transport containers 40 is held by means of a clamp 28. Clamp 28 prevents the stack of transport containers 40 from falling down into delivery conduit 33. As depicted in FIG. 7, transport holder 34 is located directly beneath the stack. Transport holder 34 is attached to transport mechanism 42 (not shown in detail) with a bracket 43. A slide 4 is located in transport container 40 that rests on transport holder 34. Multiple liquid droplets 6 are located on slide 4. In the preferred exemplary embodiment shown here, 3×8 liquid droplets 6 are arranged on slide 4. The bottommost transport container 40 is held by clamp 28 in such a way that clamp 28 engages into at least one protrusion 41 on each side of transport container 40 and holds the latter. Clamp 28 has shaped onto it at least one lug 28a that engages into the corresponding protrusion 41 on transport container 40.

Figure 9:
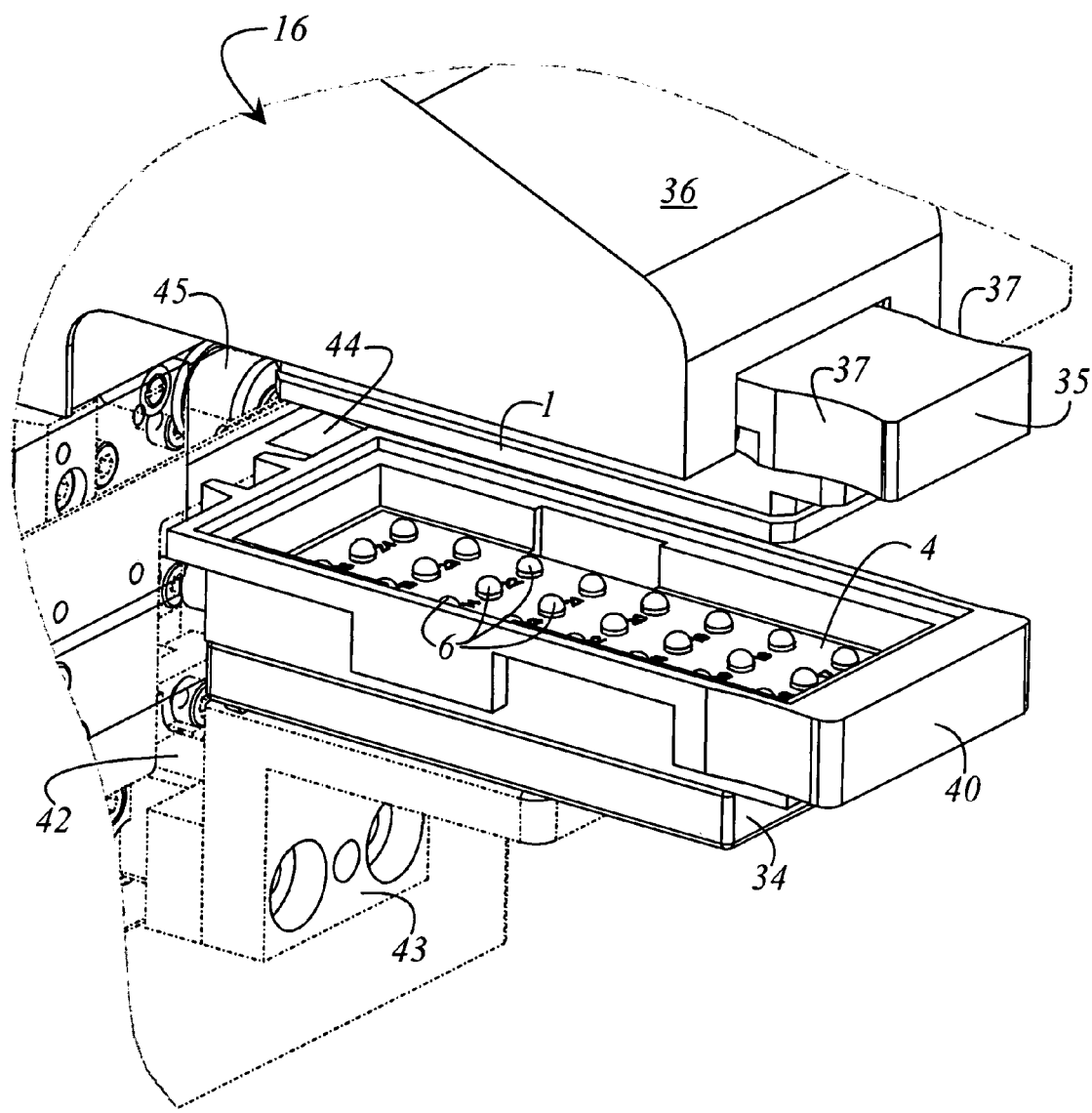
FIG. 9 is a perspective detail view of the coaction of the transport holder with a carrier plate located in the treatment section.

FIG. 9 is a perspective detail view of the coaction of transport holder 34 with a carrier plate 1 located in treatment section 16. Transport mechanism 42 and bracket 43 for retaining transport holder 34 for transport containers 40 are depicted with dashed lines. A slide 4 rests on transport holder 34. The positions of liquid droplets 6 on slide 4 located in transport container 40 correspond to the positions of metal grids 2 on carrier plate 1 (see FIG. 1). Carrier plate 1 is retained in treatment section 16 by holder 35, which is attached to arm 36 of treatment section 16. Holder 35 possesses two grip recesses 37 that are used to introduce the holder into arm 36 of treatment section 16 and/or remove it therefrom. The treatment section encompasses means (not depicted) that center the carrier plate from above laterally and in parallel fashion, so that the positions of metal grids 2 and of liquid droplets 6 coincide. Slide 4 is brought closer to carrier plate 1 by transport mechanism 42. At a specific short distance between slide 4 and carrier plate 1, liquid droplets 6 wet metal grids 2 on carrier plate 1, together with the tissue sections. This position is held constant for a certain time, the time being based on the treatment process configured by the user. The distance between carrier plate 1 and slide 4 depends on the volume of liquid droplets 6. Different volumes for the liquid droplets are advisable because on the one hand washing droplets should be as large as possible in order to achieve a good cleaning effect, while on the other hand labeling solutions with antibodies are very expensive and the volume should thus be kept as small as possible. Transport mechanism 42 can encompass a linear guidance system having a drive system using a stepping motor 45 and position sensors. In order to ensure an accurate distance between carrier plate 1 and slide 4, a sensor 44 is provided that measures the distance from carrier plate 1 to slide 4. Liquid droplets 6 are metered with a pipette so that their volume is accurately determined.

Figure 10A:
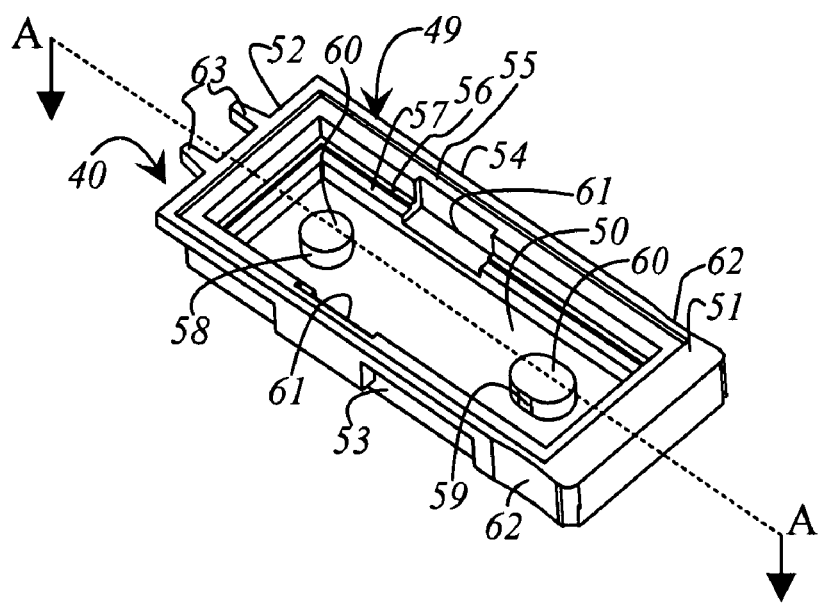
FIG. 10a is a perspective top view of an embodiment of the transport container.

A perspective top view of an embodiment of transport container 40 is depicted in FIG. 10a. Transport container 40 is embodied in the form of a trough that comprises a peripheral delimiting wall 49 which is closed off by a base 50. Transport container 40 is produced from a dimensionally stable material. As a rule, transport container 40 is produced using an injection-molding method. Other production methods, for example milling, are also conceivable, but injection molding is the most cost-effective. The material of which transport container 40 is made is a suitable polymer material (e.g. RYTON BR 111 BL of the Chevron Phillips Chemical Company). Delimiting wall 49 possesses a front wall 51 and a back wall 52, both joined to one another via a left and a right sidewall 53 and 54. Front wall 51 and back wall 52 each form a right angle with left and with right sidewall 53 and 54. Delimiting wall 49 has toward the inside a peripheral first step 55, a peripheral second step 56, and a peripheral third step 57. The next transport container 40 (see FIG. 7)

rests with its base 50 on first step 55. Base 50 of the one transport container 40 thus simultaneously constitutes a cover for the next transport container 40 located below it. Slide 4 rests on third step 57 and is simultaneously fixed in position by the edge of second step 56. Base 50 of transport container 40 has a first and a second elevation 58 and 59, each of which possesses a planar flattened area 60. Flattened area 60 is located at the height of third step 57, so that the elevations serve as supports for slide 4. First elevation 58 is round. Second elevation 59 is oval in shape. In addition, a moisture-emitting medium (not depicted in FIG. 10*a*) can be placed onto base 50 of transport container 40. Left and right sidewalls 53 and 54 each have a protrusion 61. In the region of the protrusion, slide 4 is not completely in contact against left and right sidewalls 53 and 54 so that, for example, moisture from the moisture-emitting medium on base 50 of transport container 40 can reach the surface of slide 4 that carries liquid droplets 6 (see FIG. 11). Protrusions 61 likewise facilitate the removal of slide 4 from transport containers 40. Left and right sidewalls 53 and 54 of transport container 40 possess, in the region of its front wall 51, two grip recesses 62 that make transport container 40 easier to handle for the user. Back wall 52 of transport container 40 has two parallel lugs 63 shaped onto it. Lugs 63 are embodied in such a way that they lie on either side of third bar 24*c* (see FIG. 7) of first and second stations 20 and 21 and thus represent a guide for the stack of transport containers 40.

Figure 10B:
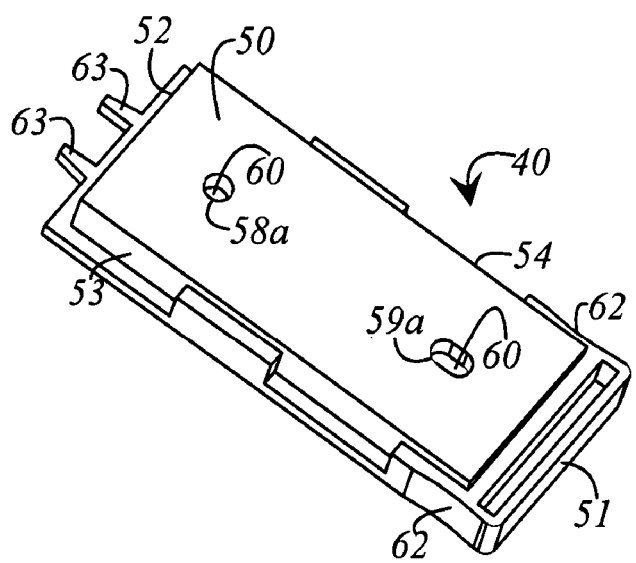
FIG. 10b is a perspective bottom view of an embodiment of the transport container.

FIG. 10*b* is a perspective bottom view of the embodiment of transport container 40 depicted in FIG. 10*a*. First and second elevations 58 and 59 are not configured in solid fashion. First elevation 58 possesses a depression having a cross section in the shape of a circle 50*a*. Second elevation 59 possesses a depression having a cross section in the shape of an elongated hole 59*a*. Both depressions end in the region of planar flattened area 60. The depressions serve to position transport container 40 on transport holder 34. Two pins (not depicted) that position transport container 40 on transport holder 34 by engagement of the pins into the depressions are shaped onto transport holder 34 for that purpose.

Figure 11:
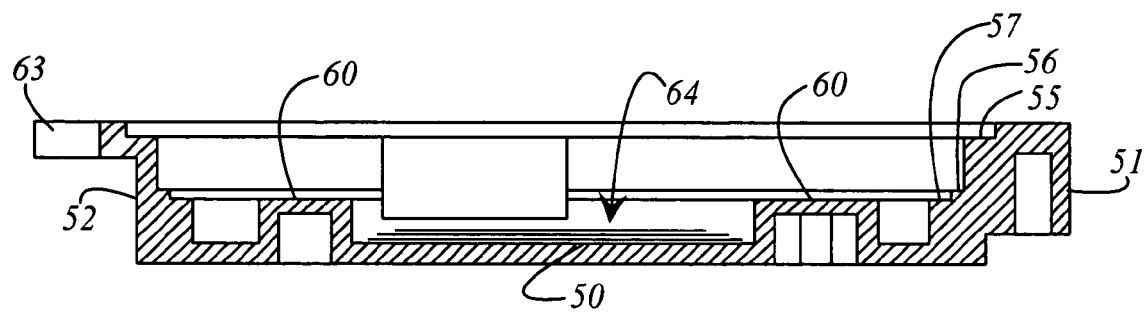

FIG. 11 is a sectioned view of transport container 40 along dashed line A—A depicted in FIG. 10*a*. It is clearly evident that third step 57 lies at the same level as flattened area 60 of first and second elevations 58 and 59. As already mentioned in the description of FIG. 10*a*, a moisture-emitting medium is provided on base 50 of transport container 40 so that the moisture prevents liquid droplets (see FIG. 9) from drying out.

Figure 12:
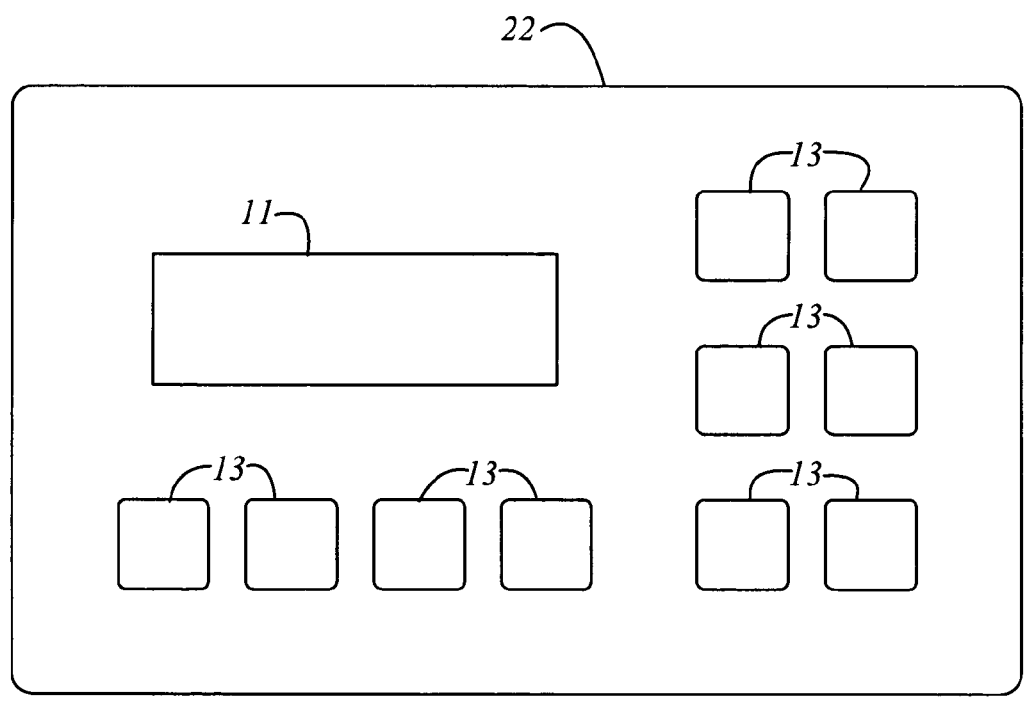
FIG. 12 is a schematic depiction of the user interface for performing inputs and configuring treatment processes.

FIG. 12 is a schematic depiction of user interface 22 for performing inputs and configuring individual treatment processes. Input buttons 13 allow the user to individually configure the treatment process that is described below.

The order of transport containers 40 in the stack that is located in first station 20 corresponds exactly to the sequence of the individual process steps. It should be noted here that slides 4 provided in the various transport containers 40 of the stack differ in each case in terms of the nature and size of liquid droplets 6 on slide 4. One slide 4 always carries liquid droplets 6 of the same size and the same type. For cost reasons, liquid droplets 6 that contain reagents for immunostaining are to be used in the smallest possible volume. In order to carry out the first process step, transport mechanism 42 travels beneath the stack of transport containers 40 present in first station 20. Transport mechanism 42 lifts the stack. Clamp 28 that holds the stack of transport containers 40 is opened, and the stack is lowered. Clamp 28 closes again at the next transport container 40. A single open transport container 40 thus rests on transport mechanism 42.

This transport container 40 is moved to treatment section 16. There transport container 40 is lifted until liquid droplets 6 on slide 4 come into contact with metal grids 2 on carrier plate 1. This distance between carrier plate 1 and slide 4 must be very accurately complied with in order to ensure on the one hand that all liquid droplets 6 contact metal grids 2, but on the other hand that the liquid of liquid droplets 6 touches only the lower side of metal grids 2. A sensor 44 that measures the distance between carrier plate 1 and slide 4 is advantageous. Liquid droplets 6 are metered with a pipette onto slide 4 at positions provided for them. Inputting of the volume of liquid droplets 6 via input buttons 13 provided on input section 12 causes the requisite parameters to be transferred to the electronic control system so that the optimum distance between metal grids 2 and slide 4 is calculated and set.

Transport mechanism 42 guides slide 4 into position beneath carrier plate 1 mounted in holder 35 (see FIG. 9). Transport mechanism 42 lifts transport container 40, together with slide 4, so that liquid droplets 6 can come into contact with the metal grids in the manner calculated by the electronic control system. After completion of the residence time (also set via input section 12) for the respective process step, transport container 40 is lowered and moved to second station 21. In second station 21, a stack of transport containers 40 containing exhausted slides 4 is built up. For this, the stack in the second station is lifted until clamp 28 is closed again and thus grips the bottommost transport container in the stack at protrusions 41 provided for the purpose. Transport mechanism 42 is lowered once again and moved beneath the first station. At the beginning of the next process step, the next transport container 40 is removed from first station 20 as already described. In FIG. 7, first station 20 is almost completely filled with transport containers 40.

The process continues until the last transport container 40 in first station 20 is reached. The procedure is programmable by the user via input section 12. For each process step, the residence time and the size of liquid droplets 6 are likewise settable via input section 12.

A multi-channel pipette 80 (see FIG. 4*b*) is used to facilitate the loading of slides 4 with liquid droplets 6. With an eight-channel pipette, for example, eight droplets of the same volume can be placed simultaneously onto slide 4 at the positions provided for them. This requires that the spacings of depressions 5 in Teflon coating 5*a* of slide 4 match the spacings of the pipette tips. This operation of applying liquid droplets 6 is thereby also made substantially easier. Numbers on Teflon coating 5*a* of slide 4 and on the carrier plate allow a unique correlation between grids and liquid droplets 6. This is necessary because a variety of immune labels are utilized in many procedures. Different reagents on one slide 4 are possible.

The apparatus according to the present invention is adapted so that it automatically performs the following steps of an already existing standard protocol for immunological labeling of thin tissue sections: saturation of nonspecific bonds, antibody incubation, and various washing steps with different washing solutions.

The invention has been described with reference to a particular embodiment. It is clear to one skilled in the art, however, that changes and modifications can be made without thereby leaving the range of protection of the claims.

The invention claimed is:

1. An apparatus for immunological labeling of thin tissue sections comprising:

an input section, a supply section, and a treatment section;

a transport mechanism which travels back and forth between the supply section and the treatment section in order to transport at least one transport container from the supply section to the treatment section or from the treatment section to the supply section;

a carrier plate positioned in said treatment section on which the thin tissue sections are affixed in a defined pattern;

at least one slide on which a treatment liquid is applied in the form of droplets, wherein the arrangement of the droplets on the slide corresponds to the arrangement of the thin tissue sections on the carrier plate;

each transport container for holding one slide; wherein the transport container has a peripheral delimiting wall attached to a base; and, said supply station comprising a first and a second station, in which the transport containers are stacked, wherein the base of one transport container constitutes the cover of a transport container arranged beneath it, wherein in the treatment section, the transport mechanism lifts the transport container in such a way that the liquid droplets present on the slide wet the tissue sections provided on the one lower side of the carrier plate.

2. The apparatus as defined in claim 1, wherein the transport containers that each carry a slide are in the first station and a plurality of fresh, unused droplets are arranged on the slides.

3. The apparatus as defined in claim 2, wherein the transport containers that each carry a slide are stacked in the second station and a plurality of droplets, already used during a treatment step are arranged on the slides.

4. The apparatus as defined in claim 1, wherein in the first station and in the second station, the topmost transport container in each case is not equipped with a slide; and the base of that transport container exclusively constitutes the cover for the following transport container in the first and second station.

5. The apparatus as defined in claim 1, wherein each of the tissue sections are on the lower side of the carrier plate and rest on a metal grid that is held in position by a magnet provided in the carrier plate.

6. The apparatus defined in claim 1, wherein the treatment section comprises an arm in which a holder for the carrier plate is retained.

7. The apparatus as defined in claim 6, wherein the holder possesses two grip recesses that serve for introduction and removal of the holder into and from the arm of the treatment section.

8. The apparatus as defined to claim 1, wherein the input section encompasses a user interface with multiple input buttons and a display.

9. The apparatus as defined in claim 1, wherein the supply section is enclosed and is accessible from outside via a first and a second door, the first station with transport containers being arranged behind the first door, and the second station with transport containers being arranged behind the second door.

10. The apparatus as defined in claim 1, wherein the treatment section has a pivotable cover beneath which a staining unit is located in which a carrier plate is retained.

11. The apparatus as defined in claim 1, wherein the first and second station are constituted by a first, second, and third bar that are parallel to one another; the first and second bar are the endpoints of the base of an isosceles triangle; the third bar is the vertex of the isosceles triangle; the first, second, and third bar serve as guides for the transport containers; and the bars are secured their upper ends in a common plate.

* * * * *